United States Patent [19]

Bilstad

[11] 4,425,113
[45] Jan. 10, 1984

[54] FLOW CONTROL MECHANISM FOR A PLASMAPHERESIS ASSEMBLY OR THE LIKE

[75] Inventor: Arnold C. Bilstad, Deerfield, Ill.

[73] Assignee: Baxter Travenol Laboratories, Inc., Deerfield, Ill.

[21] Appl. No.: 390,463

[22] Filed: Jun. 21, 1982

[51] Int. Cl.³ .......................... A61M 5/00; A61M 1/03
[52] U.S. Cl. ............................................ 604/6; 604/34; 604/250; 251/9
[58] Field of Search ..................... 604/6, 5, 4, 34, 250, 604/30; 251/4, 6, 7, 9

[56] References Cited

U.S. PATENT DOCUMENTS

| | | |
|---|---|---|
| 250,085 | 10/1878 | Tuttle . |
| 1,710,540 | 4/1929 | Hollander . |
| 2,077,774 | 4/1937 | Rudder . |
| 2,261,213 | 11/1941 | Bierman . |
| 2,485,842 | 10/1949 | Pennington . |
| 2,854,027 | 9/1958 | Kaiser et al. . |
| 3,016,915 | 1/1962 | Moeller, Jr. . |
| 3,048,192 | 8/1962 | Murphy, Jr. . |
| 3,157,201 | 11/1964 | Littmann . |
| 3,185,179 | 5/1965 | Harauteneian . |
| 3,187,750 | 6/1965 | Tenczar, Jr. . |
| 3,411,534 | 11/1968 | Rose .................................... 604/250 |
| 3,459,182 | 8/1969 | Naftulin . |
| 3,550,900 | 12/1970 | Rolin ........................................ 251/9 |
| 3,575,161 | 4/1971 | London . |
| 3,607,082 | 9/1971 | Thiers . |
| 3,610,228 | 10/1971 | Temkin . |
| 3,618,637 | 11/1971 | Santomieri . |
| 3,626,938 | 12/1971 | Versaci . |
| 3,628,813 | 12/1971 | Lee et al. . |
| 3,648,693 | 3/1972 | Koremura . |
| 3,730,170 | 5/1973 | Michael . |
| 3,747,812 | 7/1973 | Karman et al. . |
| 3,782,382 | 1/1974 | Naftulin et al. . |
| 3,783,900 | 1/1974 | Waldbillig . |
| 3,794,032 | 2/1974 | Derouineau . |
| 3,805,842 | 4/1974 | Thompson et al. . |
| 3,834,372 | 9/1974 | Turney . |
| 3,877,428 | 4/1975 | Seagle et al. . |
| 3,886,937 | 6/1975 | Bobo et al. . |
| 3,892,197 | 7/1975 | Kinney et al. . |
| 3,915,167 | 10/1975 | Waterman ........................... 604/250 |
| 3,916,948 | 11/1975 | Benjamin . |
| 3,945,380 | 3/1976 | Dabney et al. . |
| 3,957,082 | 5/1976 | Fuson et al. . |
| 3,960,224 | 6/1976 | Silvers . |
| 3,963,024 | 6/1976 | Goldowsky . |
| 3,972,350 | 8/1976 | Pickett . |
| 3,985,134 | 10/1976 | Lissot et al. . |
| 3,994,294 | 11/1976 | Knute . |
| 4,061,142 | 12/1977 | Tuttle . |
| 4,082,095 | 4/1978 | Mendelson et al. . |
| 4,126,133 | 11/1978 | Schwartz . |
| 4,282,902 | 8/1981 | Haynes ........................... 604/250 X |

FOREIGN PATENT DOCUMENTS 2509485 9/1976 Fed. Rep. of Germany ...... 604/250

Primary Examiner—Stephen C. Pellegrino
Attorney, Agent, or Firm—Paul C. Flattery; Daniel D. Ryan

[57] ABSTRACT

A flow control device includes a first member and a second member which has a movable portion. The first member accommodates the attachment of a length of flexible conduit. The second member can be positioned on the first member to sandwich the secured conduit between the first member and the movable portion of the second member. When in this position, displacement of the movable portion serves to selectively pinch close the secured conduit between the movable portion and the first member. Fluid flow through the conduit can thus be conveniently controlled. The device is extremely adaptable and can be readily incorporated into virtually any fluid system which requires complex, repetitive valving functions, such as those associated with a plasmapheresis assembly.

38 Claims, 17 Drawing Figures

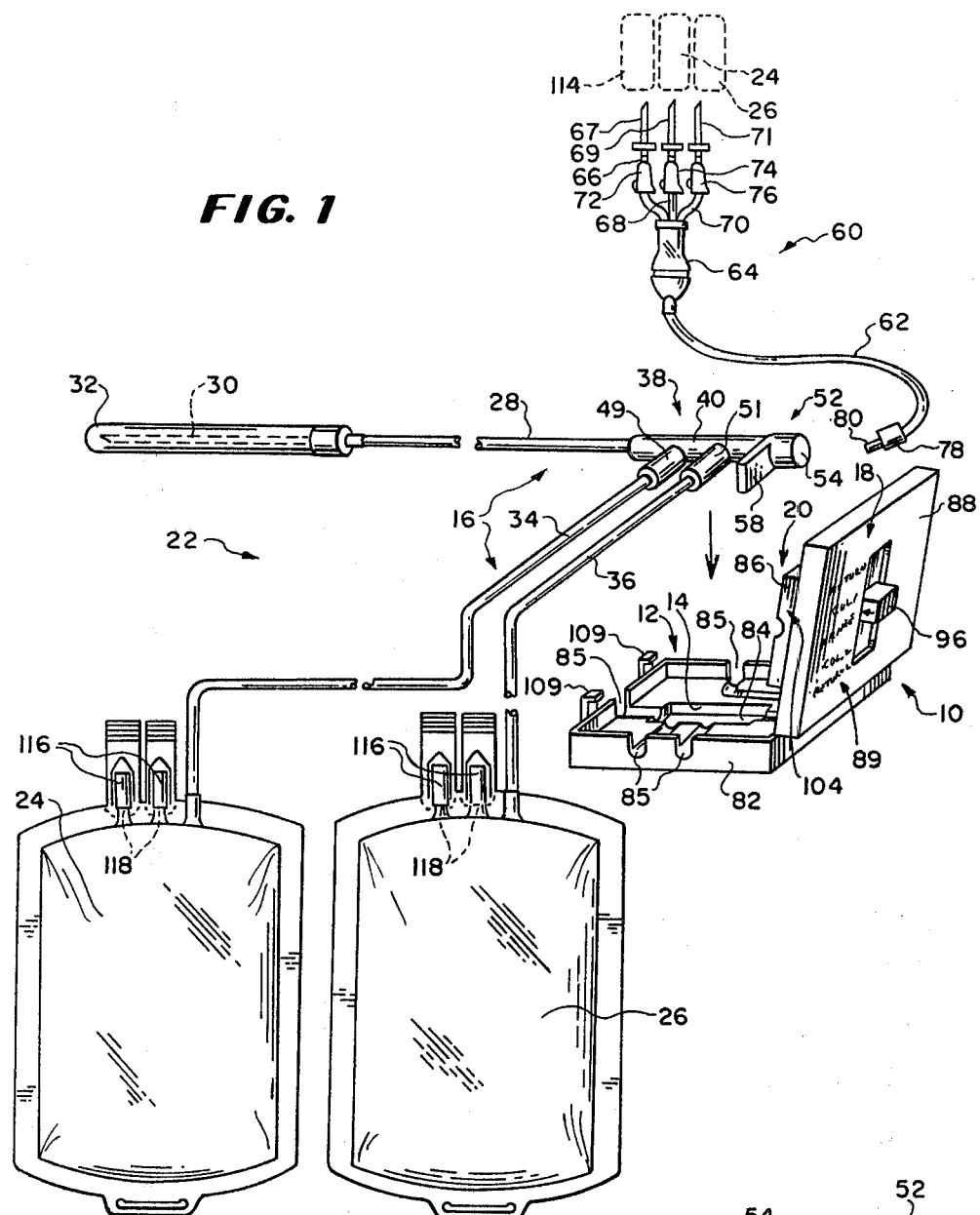
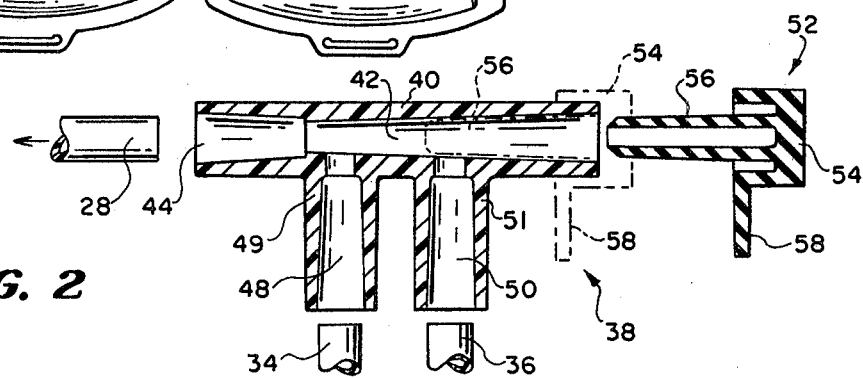
FIG. 1
FIG. 2

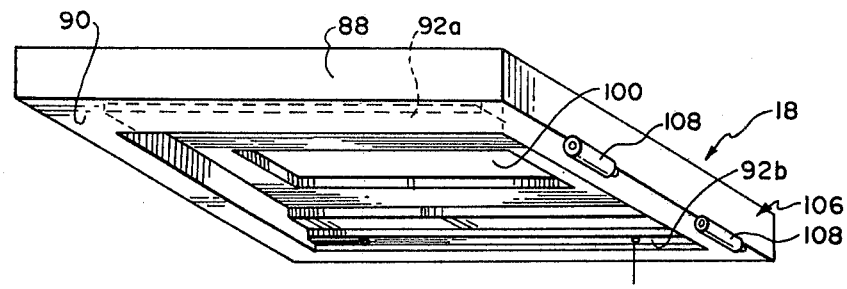
FIG. 3
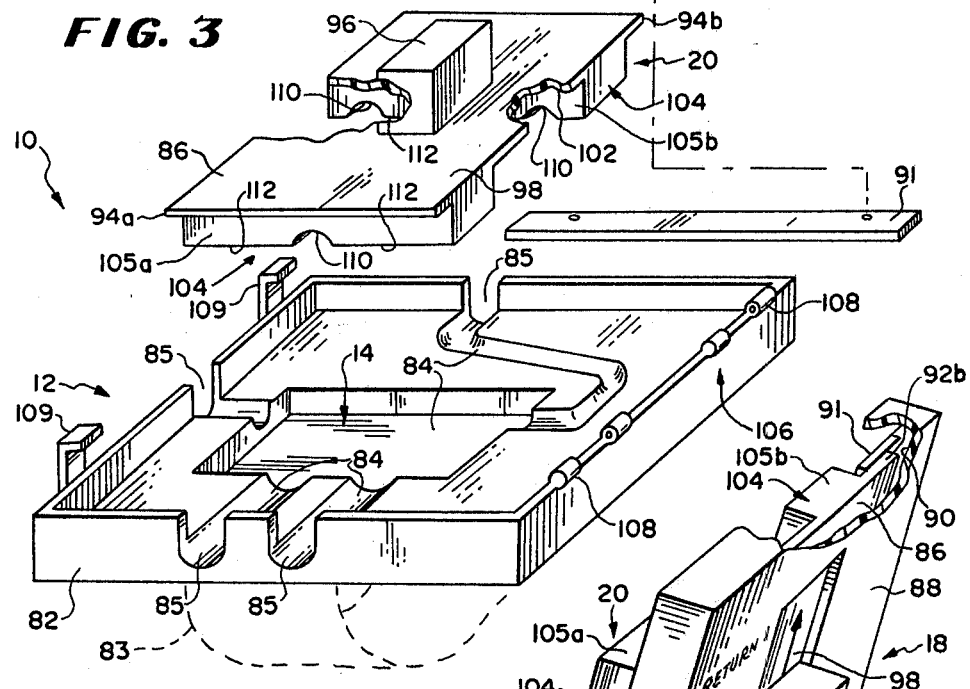
FIG. 4
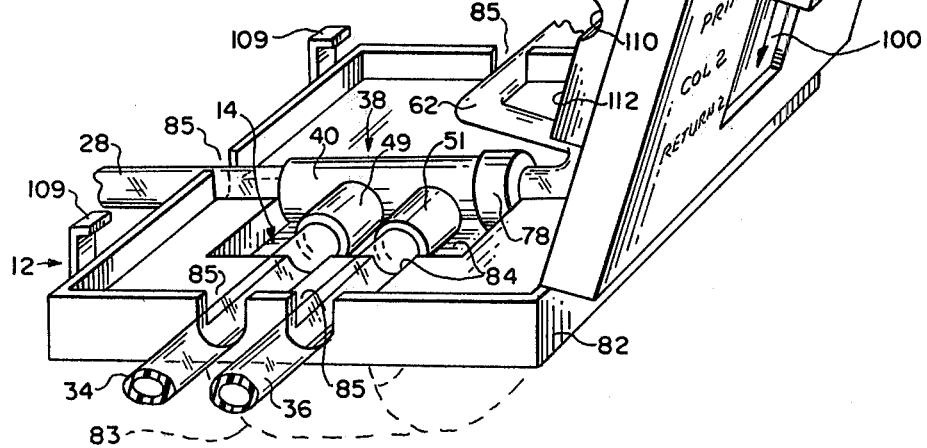

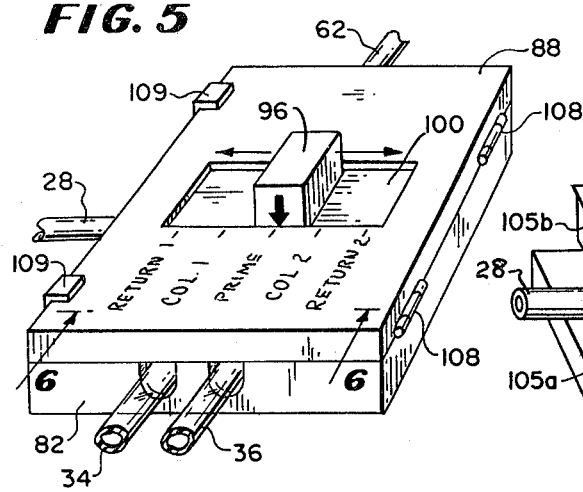
FIG. 5
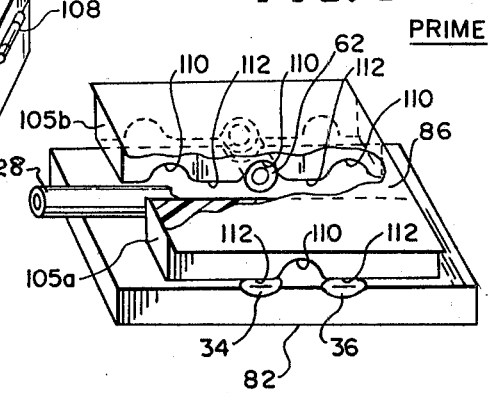
FIG. 6 PRIME
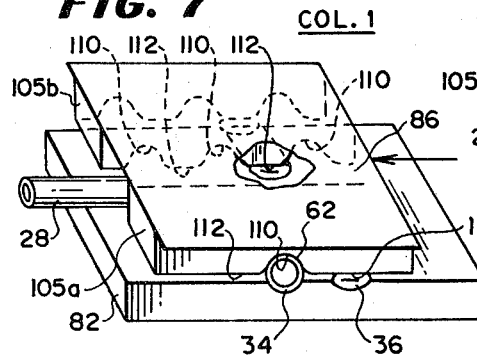
FIG. 7 COL. 1
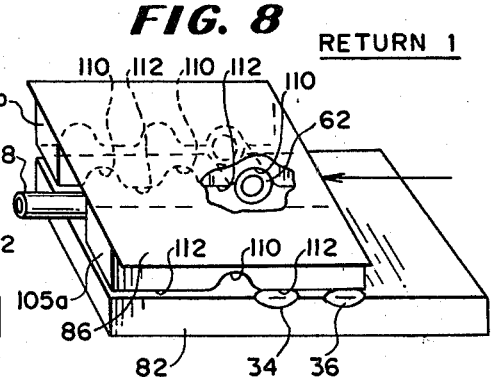
FIG. 8 RETURN 1
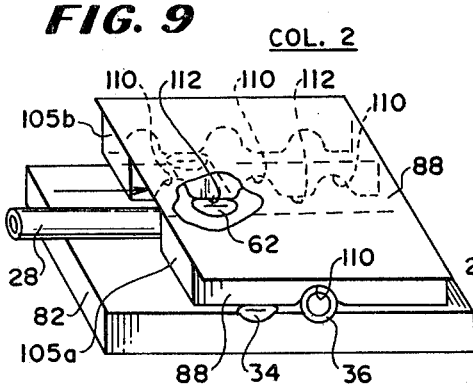
FIG. 9 COL. 2
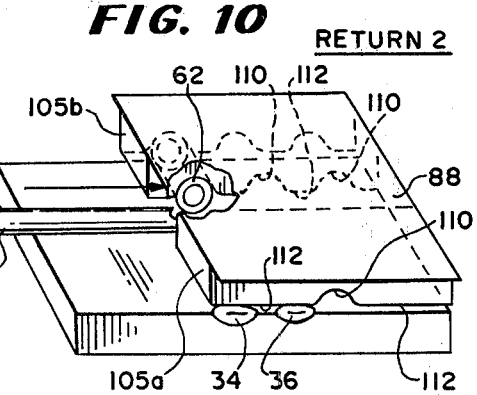
FIG. 10 RETURN 2

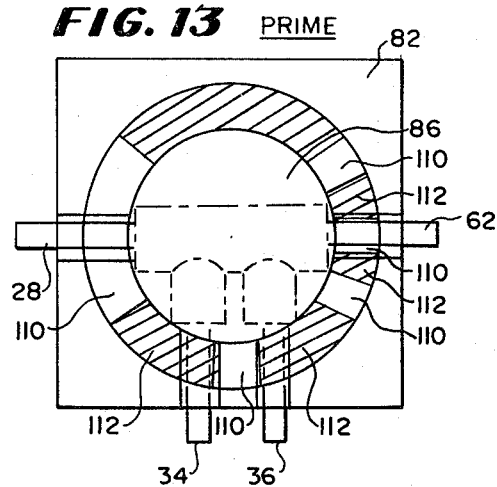
FIG. 13 PRIME
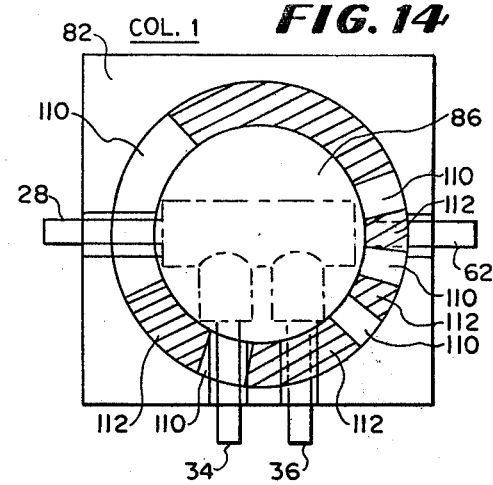
FIG. 14 COL. 1
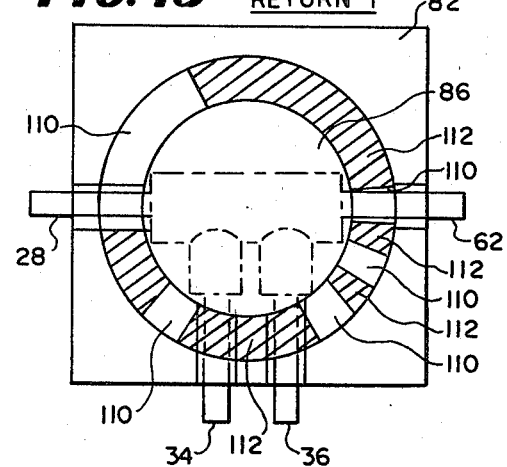
FIG. 15 RETURN 1
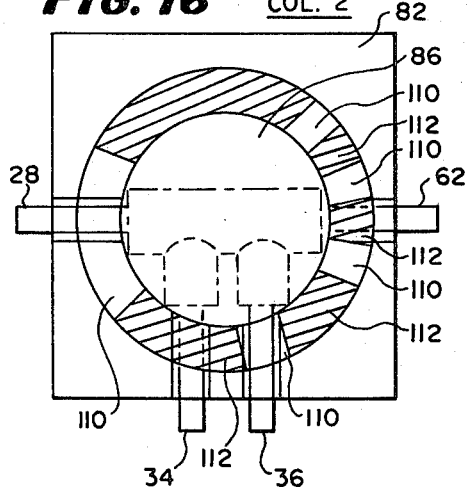
FIG. 16 COL. 2
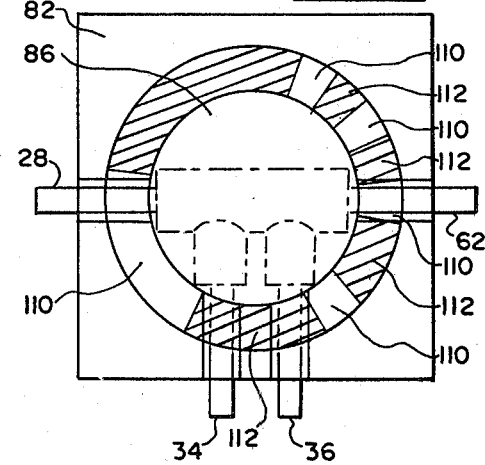
FIG. 17 RETURN 2

FLOW CONTROL MECHANISM FOR A PLASMASPHERESIS ASSEMBLY OR THE LIKE

FIELD OF THE INVENTION

The invention generally relates to fluid control devices. The invention also generally relates to plasmapheresis apparatus and processes.

BACKGROUND AND OBJECTS OF THE INVENTION

Plasmapheresis is a procedure which facilitates the collection of source plasma for commercial fractionation into antihemophiliac factor (AHF), albumin, and other plasma protein fractions. During conventional plasmapheresis, a unit of whole blood is collected and separated into red cells and plasma. The red cells are returned to the donor, and the plasma is retained for fractionation purposes. Another unit of whole blood is then drawn from the donor utilizing the same phlebotomy, and the whole blood is again separated into red cells and plasma. As before, the red cells are returned to the donor, and only the plasma is retained. The end result is, for each plasmapheresis procedure, two units of source plasma for fractionation purposes.

Representative examples of disposable plasmaphersis assemblies include the following United States Patents No.:
Naftulin: 3,459,182
Naftulin et al: 3,782,382
Dabney: 3,945,380

Representative examples of known, commercially available disposable plasmapheresis assemblies include those sold by Fenwal Laboratories (a division of Travenol Laboratories, Inc., Deerfield, Ill.); Cutter Laboratories, Inc., (Berkely, Calif.); Delmed Corp. (Irvine, Calif.); and Terumo Company, Ltd., (Japan).

The nature of a typical plasmapheresis procedure demands the use of clamping devices which selectively control the flow of blood and components through a given plasmapheresis assembly. Typically, several manually actuated clamping devices, such as hemostats and/or roller clamps, are used in tandem for this purpose. Use of such devices entails multiple clamping arrangements and time consuming manipulations during the procedure. The devices also introduce the possibility of operator error.

The plasmapheresis assembly discussed in the above-cited Naftulin et al document uses a manifold to interconnect the blood collection containers with the needle. The flow of fluids through the manifold is controlled by the use of inline ball valves. Such an inline valving arrangement, however, does not facilitate repetitive valving functions, because, once a ball valve is squeezed out of the fluid path to open low communication, it cannot be easily returned to subsequently close flow communication. Furthermore, such an inline valving arrangement introduces a potentially leak-prone device into the flow paths of the assembly.

Attention is also directed to copending Ronald A. Williams U.S. patent application entitled FLOW CONTROL MECHANISM FOR A PLASMAPHERESIS ASSEMBLY OR THE LIKE, Ser. No. 390,464, which shares the same filing date and assignee as this application.

It is one of the principal objects of this invention to provide a fluid control assembly which performs multiple, repetitive valving operations to establish a plurality of flow modes in a given fluid circuit, such as a plasmapheresis assembly, without introducing complicated and/or leak-prone devices into the fluid circuit.

It is another one of the principal objects of this invention to provide a fluid control assembly which can be utilized to control the flow of fluids through a given fluid circuit, such as a plasmapheresis assembly, from a convenient centralized location, thereby reducing, as much as possible, the number of clamping manipulations required to operate the fluid circuit, and thereby minimizing, as much as possible, the chance of operator error.

It is yet another one of the principal objects of this invention to provide a fluid control assembly which can be readily incorporated into a given fluid circuit, including one utilized for plasmapheresis, without entailing major modifications to the circuit.

SUMMARY OF THE INVENTION

To achieve these and other objects, the invention provides a flow control device for a flexible conduit. The device comprises a first member to which a length of flexible conduit can be releasably secured. The device also includes a second member having a movable portion. Means is provided for mounting the second member in an operative position on the first member. When the second member is in this operative position, the secured conduit is located between the first member and the movable portion of the second member. Subsequent displacement of the movable portion serves to selectively pinch close the secured conduit between the movable portion and the first member.

In one embodiment, the movable portion includes cam means. When the movable portion is displaced toward one position, the cam means is operative for engaging the secured conduit. The engaged conduit is pinched close between the cam means and the first member, preventing fluid flow through the conduit. When the movable portion is subsequently displaced toward the another position, the cam means is operative for disengaging the conduit, allowing the conduit to resiliently return to a normal position open to fluid flow.

In one embodiment, the movable portion of the second member is operative for displacement transversely of the remaining portion of the second member. In another embodiment, the movable portion of the second member is operative for rotation relative to the remaining portion.

In one embodiment, the movable portion of the second member includes a platen, and the remaining portion includes a housing on which the platen is movably mounted. In this embodiment, the housing is hingedly attached to the first member for movement between an inoperative position, in which the movable platen is generally disposed away from the first member to allow the conduit to be releasably secured to the first member, and the heretofore described operative position, in which the secured conduit is sandwiched between the movable platen and the first member.

In one embodiment, at least two lengths of flexible conduit can be releasably secured on the first member. In this embodiment, the movable portion of the second member is operative for selectively pinching close one or more of the secured conduits in a predetermined sequence.

The invention also provides a plasmapheresis assembly which includes the flow control device as above generally described. In one embodiment, the assembly includes a manifold which interconnects auxiliary conduits associated with a pair of blood collection containers with a primary conduit having, at one end, a phlebotomy needle. In this arrangement, the manifold, as well as the connected conduit, can be releasably secured to the first member of the fluid control device. When the second member is disposed in its operative position, displacement of its movable portion serves to selectively control the flow of blood and blood components between the phlebotomy needle and each of the blood collection containers. Successive displacement of the movable portion serves to establish a predetermined sequence of flow patterns which facilitate the plasmapheresis procedure.

The fluid control assembly which embodies the features of the invention can handle complex, repetitive valving operations, such as those associated with a plasmapheresis procedure, and does not constitute a leak-prone device disposed in the flow path. The assembly is straightforward in construction and operation and can be readily incorporated into virtually any fluid system with only minimal modifications to the system.

Other features and advantages of the invention will be pointed out in, or will be apparent from, the specification and claims, as will obvious modifications of the embodiments shown in the drawings.

DESCRIPTION OF THE DRAWINGS

FIG. 1 is a perspective view of a plasmapheresis assembly which includes a flow control device which embodies various features of the invention;

FIG. 2 is an enlarged and exploded view of the manifold which is associated with the flow control assembly shown in FIG. 1;

FIG. 3 is an exploded perspective view, with portions broken away and in section, of the flow control device shown in FIG. 1;

FIG. 4 is an assembled perspective view, with portions broken away and in section, of the flow control device shown in FIG. 3 in an inoperative position and with the manifold associated with the plasmapheresis assembly releasably secured thereto;

FIG. 5 is a perspective view of the flow control device shown in FIG. 4 in an operative position;

FIGS. 6 through 10 are perspective, diagrammatic views of the interior of the flow control device taken generally along line 6—6 in FIG. 5 with the movable platen disposed in different operative positions;

FIGS. 13 through 17 are diagrammatic views of the interior of the flow control device shown in FIGS. 11 and 12 looking generally downwardly upon the housing with the housing in its operative position and with the movable platen disposed in different operative positions.

Figure 11:
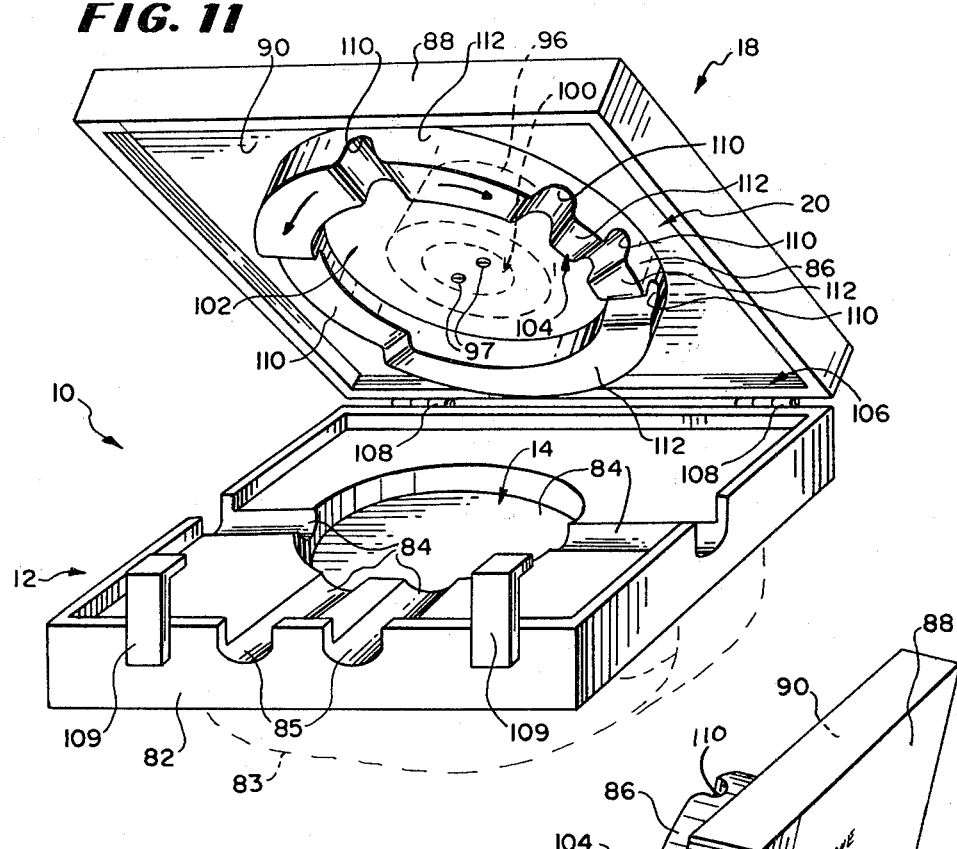
FIG. 11 is a perspective view of another embodiment of a flow control device which embodies features of the invention and which is shown in its inoperative position.

Before explaining the embodiments of the invention in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

DESCRIPTION OF THE PREFERRED EMBODIMENTS

A flow control device 10 which embodies various features of the invention is shown in FIG. 1.

Generally, as shown in FIG. 1, the device includes a first member 12 which includes means 14 for releasably securing thereon one or more lengths of flexible conduit 16.

Use of the term "flexible" herein signifies that the conduit or tubing has resiliently deformable sidewalls which can be pinched or crimped together in response to an external force, thereby occluding and closing the fluid path through the conduit or tubing, and which are capable of resiliently returning to a normally open position when the external force is removed.

The device 10 also includes a second member 18 having a movable portion 20. As will be described in greater detail later herein, when the second member 18 is mounted in a predetermined operative position upon the first member 12, displacement of the movable portion 20 of the second member 18 serves to selectively crimp or collapse at least one of the flexible conduits 16 secured to the first member 12. The device 10 therefore enables the flow of fluids into and through the secured conduits 16 to be controlled from a convenient, centralized location.

It will be appreciated that the fluid control device 10 of this invention can be readily incorporated into virtually any fluid network having flexible conduits 16. However, in the detailed description which follows, the construction and operation of the device 10 will be explained in the context of its use in association with a plasmapheresis assembly 22. Nevertheless, the adaptability of the fluid flow control device 10 for use in diverse other operative environments should be kept in mind.

As shown in FIG. 1, the plasmapheresis assembly 22 includes first and second whole blood collection containers, respectively 24 and 26. The containers 24 and 26 each typically takes the form of a bag fabricated from a plastic material, such as plasticized medical grade polyvinyl chloride.

The conduits 16 associated with the plasmapheresis assembly 22 include a length of flexible tubing 28. This length of tubing 28 will hereafter be referred to as the primary tubing of the assembly 22.

A phlebotomy needle 30 is attached in flow communication with one end of the primary tubing 28. A removable needle cover 32 of conventional construction (see, for example, Bellamy Jr., U.S. Pat. No. 3,123,072) normally seals the needle 30 from communication with the atmosphere until venipuncture is made.

The conduits 16 of the plasmapheresis assembly 22 further include first and second auxiliary tubings, respectively 34 and 36, which communicate with the containers 24 and 26.

The conduit securing means 14 of the device 10 can be variously configured to accommodate each length of tubing 28, 34, and 36, or comparable fluid conduits 16. However, in the preferred embodiment, manifold means 38 is provided to interconnect both the containers 24 and 26 in flow communication with the phlebotomy needle 30. The manifold means 38 serves to reduce the overall complexity of the fluid circuit associated with the assembly 22 and, in doing so, facilitates the mounting of the tubings 28, 34, and 36 on the first member 12.

The manifold means 38 itself may be variously constructed. However, in the illustrated embodiment, the manifold means 38 is generally constructed along the lines disclosed in copending Nevens et al, U.S. patent application No. 300,338, filed Sept. 8, 1981, and entitled PLASMAPHERESIS ASSEMBLY AND ASSOCIATED FLUID MANIFOLD.

More particularly, and as can be best seen in FIG. 2, the manifold means 38 includes a tubular main body 40 through which a main passage 42 extends. The main passage 42 has axially spaced first and second end portions 44 and 46.

Still referring principally to FIG. 2, a pair of branch passages 48 and 50 communicates with the main passage 42. One branch passage 48 (hereafter referred to as the first branch passage) is disposed generally adjacent to the end portion 44. The other branch passage 50 (hereafter referred to as the second branch passage) is disposed generally adjacent to the other end portion 46.

In the illustrated embodiment, each branch passage 48 and 50 extends within a tubular body 49 and 51. The tubular bodies 49 and 51 extend in a spaced-apart parallel fashion outwardly from the same side of the manifold main body 40.

As can be seen in FIGS. 1 and 2, the end of the primary tubing 28 opposite to the phlebotomy needle 30 is bonded, such as by solvent sealing, within the end portion 49 of the manifold main passage 42. Likewise, the first and second auxiliary tubings 34 and 36 are also attached, such as by solvent sealing, in flow communication with the first and second branch passages 48 and 50.

The manifold means 38 further includes plug means 52 which is removably insertable into the end portion 46 of the main passage 42, as is shown in solid lines in FIG. 1 and in phantom lines in FIG. 2.

In the illustrated embodiment, the plug means 42 includes a cap portion 54, which is formed to fit snugly in a fluid-tight relationship about the exterior of the end portion, and a stem portion 56, which is formed to extend axially into and in a fluid-tight relationship within the main passage 42 (as shown in phantom lines in FIG. 2). In the illustrated and preferred embodiment, the cap portion 54 includes a tab 58 which can be grasped between the fingers of the operator to facilitate removing the cap portion 54 from its snug engagement on the end portion 46.

As is best shown in phantom lines in FIG. 2, when the plug means 52 is positioned on the end portion 46 of the main passage 42, the cap portion 54 sealingly closes the end portion 46, and the stem portion 56 sealingly closes the second container 26 from communication with the main passage 42. However, at the same time, communication between the first container 24 and the main passage 42 is unimpeded.

When so positioned, the plug means 52 serves to prevent the loss or intermixing of anticoagulant solution (not shown), which is typically provided in measured amounts in each container 24 and 26 to prevent blood clotting during the plasmapheresis procedure.

As can be seen in FIG. 2, the plug means 52 can be removed, when desired, to accommodate the connection of a recipient set 60 or the like (see FIG. 1) to the plasmapheresis assembly 22. As will be described in greater detail later, the recipient set 60 allows the introduction of saline or similar I.V. solution and the return of some of the components during the course of the plasmapheresis procedure.

The recipient set 60 can be variously constructed. However, in the embodiment illustrated in FIG. 1, the set 60 includes a length of flexible tubing 62 and an inline combination filter and drip chamber 64. Upstream of the filter/drip chamber 64 are three individual inlet lines 66, 68, and 70, each having a spiked end portion, respectively, 67, 69, and 71. Roller clamps 72, 74, and 76 are provided inline with the inlet lines 66, 68, and 70 to control the fluid flow therethrough.

The tubing 62 of the recipient set 60 can be connected to the end portion 46 of the main passage 42, after the plug means 52 is removed, by means of a coupling member 78. The coupling member 78 is fabricated to include an end portion 80 which is insertable into a fluid-tight interference fit relationship into the main passage 42 through the end portion 46. The end portion 80 of the coupling member 78 is purposefully sized to occupy only a portion of the main passage 42 intermediate the junction of the second branch passage 50 and the end portion 46.

Reference is now made to the particulars of the fluid flow device 10 which is associated with the plasmapheresis assembly 22 and which embodies the features of the invention. While the flow control device 10 as heretofore described may be variously constructed, two representative embodiments of the device are shown, respectively, in FIGS. 3 through 10 and FIGS. 11 through 17.

Reference is first made to the embodiment shown in FIGS. 3 through 10. This embodiment also generally corresponds with the embodiment shown in FIG. 1. As best shown in FIGS. 3 and 4, the first member 12 takes the form of a lightweight, compact base 82. The base 82 may be constructed of a lightweight rigid plastic material utilizing injection molding techniques. It may also be formed of a lightweight metal.

Because of its compact size, the base 82 may include a wrist strap 83 (shown in phantom lines in FIGS. 3 and 4), so that the base 82 can be conveniently worn on the wrist of the donor. Alternately, the base 82 could be either temporarily or permanently attached to a suitable support frame (not shown) in the vicinity of the donor.

In this operative environment, the means 14 for securing the tubings 28, 34, 36, and 62 on the first member 12 serves also to secure the manifold means 38 on the first member 12. The means 14 may be variously constructed. In the illustrated embodiment, the means 14 takes the form of an indentation 84 which is pre-formed in the base 82. As is shown in FIG. 4, the indentation 84 is purposefully configured to accommodate the manifold means 38 and the attached primary, auxiliary, and recipient set tubings 28, 34, 36, and 62 in a desired arrangement on the base 82. As will soon become apparent, this desired arrangement positions the tubings 28, 34, 36, and 62 for the desired interface with the movable portion 20 on the first member 18.

Preferably (as shown in FIG. 4), the plug means 52 is removed and the recipient set 60 is attached to the manifold means 38 prior to the mounting of the manifold means 38 on the base 82.

The means 14 also includes openings 85 which accommodate an inimpeded, straight-line passage of the tubings 28, 34, 36, and 62 outwardly beyond the base 82 (see FIG. 4).

In this embodiment, the movable portion 20 of the second member 18 takes the shape of a generally rectilinear platen 86. The remaining portion of the second member 18 includes a housing 88 in which the platen 86 is movably mounted.

More particularly, the housing 88 includes an underbody 90 in which a spaced pair of transverse channels 92a and b are formed. The platen 86 includes side edges 94a and b which are received, respectively, within the confines of the channels 92a and b for sliding movement therein. While various attachment methods can be used, in the illustrated embodiment (see, in particular, FIGS. 3 and 4), the channel 92a is integrally formed in the underbody 90 of the housing 88, and the channel 92b is formed between the underbody 90 an an attachable bracket member 91 which sandwiches the side edge 94b therebetween.

An upstanding control member 96 projects from the top surface 98 of the platen 86. When the platen 86 is mounted in the channels 94a and b, the control member 96 extends through an elongated opening 100 in the housing 88 (see FIG. 4). The operator is thus able to slidingly displace the platen 86 back and forth between spaced positions on the housing 88 (as generally shown by arrows in FIG. 4).

Means 106 is provided for mounting the housing 88 on the base 82 so that the desired operative interface between the platen 86 and the base 82 can be achieved. In this operative position, which is shown in FIG. 5, the tubings 28, 34, 36, and 62 which are secured to the base 82 are located between the base 82 and the underbody surface 102 of the platen 86 (see, also, FIGS. 6 through 10).

Preferably, the mounting means 106 is also operative for permitting movement of the housing 88 into an inoperative position, which is shown in FIG. 4, in which the platen 82 faces away from the base 82. The loading and unloading of the manifold means 38 and associated tubings 28, 34, 36, and 62 on the base 82 is facilitated when the housing 88 is in the inoperative position.

While the mounting means 106 may be variously constructed, in the illustrated embodiment, the mounting means 106 takes the form of a hinge 108 which attaches the housing 88 on the base 82 for movement between the inoperative position (as shown in FIG. 4), in which the housing 88 and movable platen 86 is generally disposed at a right angle to the base 82, and the operative position (as shown in FIG. 5), in which the movable platen 86 is located generally parallel to the base 82, and the tubings 28, 34, 36, and 62 are sandwiched between the platen underbody 102 and the base 82.

Resilient locking members 109 or the like are preferably provided to releasably lock the housing 88 in its operative position.

The platen 86 includes cam means 104 on its underbody surface 102. When the housing 88 is in its operative position, the cam means 104 is operative during displacement of the platen 86 for selectively engaging and disengaging one or more of the tubings secured to the base 82. When the tubing is engaged, it is pinched between the cam means 104 and the base 82. The engaged tubing is thereby crimped close. When the tubing is not engaged by the cam means 104, the tubing resiliently returns to its normal position which is open to fluid flow.

The cam means 104 may be variously constructed. In the illustrated embodiment, the cam means 104 includes an arcuate first surface area 110 which, when the housing 88 is in its operative position, is spaced away from the base 82 at a distance which exceeds the outside diameter of the tubing. When the tubing and the first surface area 110 are in vertical alignment (as shown, for example, with respect to tubing 62 in FIG. 6), the cam means 104 is in the heretofore described disengaged position with the tubing, and the tubing is open to fluid flow.

In the illustrated embodiment, the cam means 104 also includes an arcuate second surface area 112 which, when the housing 88 is in its operative position, is spaced from base 82 at a distance which is significantly less than the outside diameter of the tubing. When the tubing and the second surface area 112 are in vertical alignment (as shown, for example, with respect to tubings 34 and 36 in FIG. 6), the cam means 104 is in the heretofore described engaged position with the tubing, pinching close the tubing.

As is generally shown in FIGS. 7 through 10, by purposefully prepositioning the first and second suface areas 116 and 112 along the underbody surface 102 of the platen 86, and by correlating these positions with the position of the platen 86 relative to the housing 88, the desired fluid flow patterns into and through the manifold means 38, or any comparable fluid network connected to the base 82, can be established.

The cam means 104 may be variously arranged according to the particular operative objectives of the device 10. In the illustrated embodiment, it is desired to individually pinch close the auxiliary tubings 34 and 36 and the recipient set tubing 62, but not the primary tubing 28. To meet this objective the cam means 104 includes a first cam member 105a, which extends downwardly from the underbody surface 102 of the platen 86 generally adjacent to the side edge 94a, and a second cam member 105b, which extends downwardly from the underbody surface 102 generally adjacent to the side edge 94b.

As can be seen in FIGS. 6 through 10, when the housing 88 is in its operative position, the cam member 105a is situated in an operative interface with the auxiliary tubings 34 and 36, and the cam member 105b is situated in an operative interface with the recipient set tubing 62. Movement of the platen 86 transversely of the housing 88 serves to move the cam members 105a and b transversely of the axis of the associated tubings 34, 36, and 62.

Because it is not desired in the illustrated embodiment to pinch close the primary tubing 28, there is no cam member 105 associated with the primary tubing 28. However, in other environments in which closure of a comparable tubing is desired, the cam means 104 could be configured to accomplish this objective.

In a plasmapheresis procedure, five major operative steps are typically performed. Therefore, in the illustrated embodiment, five separate operative positions of the platen 86 are desired, and indicia 89 is provided (see FIGS. 4 and 5) to designate these operative positions for the convenience of the operator.

More particularly, the indicia 89 identify a PRIME mode; a COLLECT 1 and a COLLECT 2 mode (designated, respectively, COL. 1 and COL. 2 in FIGS. 4 and 5); and an IRRIGATE/RETURN 1 and an IRRIGATE/RETURN 2 mode (designated, respectively, RETURN 1 and RETURN 2 in FIGS. 4 and 5).

To correlate the cam members 105a and 105b with the fluid flow pattern desired for each position, the first cam member 105a includes a second surface area 112 along a majority of its length, except for a first surface area 110 interposed generally in the midsection of the length.

Furthermore, the second cam member 105b includes an alternating array of first and second surface areas 110 and 112 (as best seen in FIG. 6), with the middle first surface area 110 of the second cam member 105b generally transversely aligned with the first surface area 110 of the first cam member 105a.

The particular operation of the device 10 shown in FIGS. 3 through 10 will be described in greater detail after a description of the construction of the alternate embodiment shown in FIGS. 11 through 17.

The embodiment shown in FIGS. 11 through 17 shares many of the features shown in the heretofore described embodiment, and common elements are therefore assigned common reference numerals.

Like the first-described embodiment, the first member 12 takes the shape of a base 82 having an indentation 84 and openings 85 which together releasably receive the manifold means 38 and attached tubings 28, 34, 36, and 62 in the desired arrangement on the base 82.

Also like the first-described embodiment, the second member 18 takes the form of a housing 88 and a platen 86 which is movably mounted on the housing 88. However, unlike the first-described embodiment, in which the platen 86 is movable in a transverse direction relative to the housing 88, in the second embodiment, the platen 86 is rotatably mounted on the housing 88.

More particularly, the platen 86 in the second embodiment is generally circular in configuration. The control member 96, which is also generally circular in configuration, is coupled to the top surface 98 of the platen 86, such as by the use of screws 97 which extend through the opening 100 in the housing 88. Rotation of the control member 96 either clockwise or counterclockwise (as shown by arrows in FIG. 12) serves to rotate the platen 86 relative to the housing 88.

In this arrangement, the first and second surface areas 110 and 112 of the cam means 104 are purposefully spaced at predetermined arcuate intervals along the outer periphery of the underbody surface 102 of the circular platen 86, so as to come into vertical alignment with one or more of the selected tubings secured to the base 82 in response to rotation of the platen 86. When the tubing is in vertical alignment with one of the first surface areas 110, the tubing is open in the identical manner as heretofore described and as shown in FIGS. 6 through 10. When the tubing is in vertical alignment with one of the second surface areas 112, the tubing is pinched closed between the second surface area 112 and the base 82 in the identical manner as heretofore described and as shown in FIGS. 6 through 10.

As in the first-described embodiment, indicia 89 are provided (see FIG. 12) to designate the heretofore described five operative modes associated with the plasmapheresis procedure. The indicia 89 correlate the position of the platen 86 with the position of the cam means 104 to bring the surface areas 110 and 112 into the desired alignment with the tubings.

Reference is now made to FIGS. 6 through 10 and to FIGS. 13 through 15 and to the operation of the first and second embodiments of the device 10 in the context of a typical plasmapheresis procedure.

Figure 12:
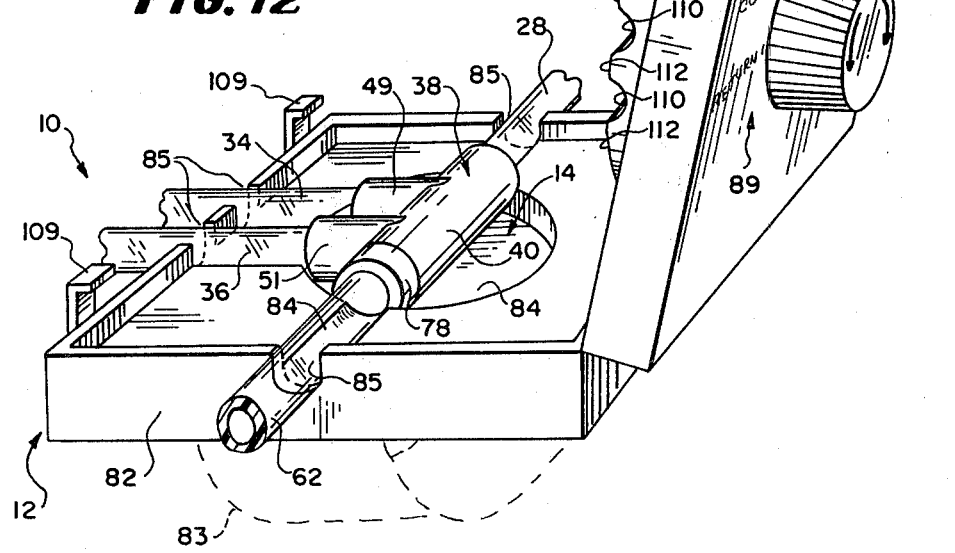
FIG. 12 is a perspective view of another side of the flow control device shown in FIG. 11 with the manifold associated with the plasmapheresis assembly releasably secured on the device.

Prior to commencing the plasmapheresis procedure, the plug means 52 is preferably removed and the recipient set 60 attached to the manifold means 38. With the housing 88 disposed in its inoperative position (as shown in FIGS. 4 and 12), the manifold means 38 and each associated tubing 28, 34, 36, and 62 can be conveniently loaded into the indentation 84 and through the openings 85 in the base 82. Movement of the housing 88 into its operative position situates the tubings 28, 34, 36 and 62 between the movable platen 86 and the base 82. The locking mechanisms 109 lock the housing 88 in its operative position.

The platen 86 is first situated in the position identified in FIGS. 4 and 12 as the PRIME mode. As can be seen in FIGS. 6 and 13, when the platen 86 is in the PRIME mode, one of the first surface areas 110 of the cam means 104 is positioned in vertical alignment with the recipient set tubing 62 and (in the second embodiment) with the primary tubing 28. In the first embodiment, there are no cam means 104 associated with the primary tubing 28 in all operative positions of the platen 86. Furthermore, when the platen 86 is in the PRIME mode, one of the second surface areas 112 is vertically aligned with each of the auxiliary tubings 34 and 36. Both of the auxiliary tubings 34 and 36 are thereby pinched closed, while both the primary tubing 28 and the recipient set tubing 62 are open.

With all of the roller clamps 72, 74, and 76 associated with the recipient set 60 initially closed (see FIG. 1), the spiked end portion 67 of one of the inlet lines 66 can be inserted into the outlet port of a conventional saline or similar I.V. container 114 (shown in phantom lines in FIG. 1). The roller clamp 72 can then be opened to prime the filter/drip chamber 64, the manifold means 38, and the opened tubings 28 and 62. Any flow of saline into the containers 24 and 26 while the platen 86 is in the PRIME mode is blocked because the auxiliary tubings 34 and 36 are pinched closed.

Once the plasmapheresis assembly has been suitably primed, the roller clamp 72 is closed. The platen 86 is next moved (to the left in the FIGS. 3 through 10 embodiment and counterclockwise in the FIGS. 11 through 17 embodiment) to the position identified as the COL. 1 (i.e., COLLECT 1) mode. As can be seen in FIGS. 7 and 14, when the platen 86 is in the COL 1 mode, the auxiliary tubing 34 (associated with the first container 24) is placed in vertical alignment with one of the first surface areas 110 of the cam means 104, opening the tubing 34. The other auxiliary tubing 36 (associated with the second container 24), the recipient set tubing 62, and (in the second embodiment) the primary tubing 28 are each simultaneously disposed in vertical alignment with selected ones of the second surface areas 112, pinching close these tubings. After the venipuncture is made, blood is directed from the donor only into the first container 24 (see also FIG. 1).

After a unit of whole blood has been collected in the first container 24, the first auxiliary tubing 34 is typically sealed closed, such as by the use of a spaced-apart of hand seal clips (not shown), or by the formation of a hermetic, snap-apart seal using a HEMATRON® dielectric sealer (also not shown), sold by the Fenwal Division of Travenol Laboratories, Inc. The first auxiliary tubing 34 can then be severed between the hand seal clips or along the snap-apart seal to separate the first container 24 from the assembly 22.

The separated first container 24 is placed in a centrifugation device (not shown) to separate the whole blood into plasma and red cells. The plasma is expressed from the container 24 by known manual or automatic means and collected for fractionation, leaving the red cells in the container 24.

During the time the whole blood in the first container 24 is being processed, it is desirable to introduce a flow of saline or similar I.V. solution through the manifold means 38 and primary tubing 28 to flush traces of blood from the flow paths and to maintain the patency of the needle 30. To accomplish this, the platen 86 is again moved (further to the left in the FIGS. 3 through 10 embodiment and further counterclockwise in the FIGS. 11 through 17 embodiment) to the position identified as the RETURN 1 (i.e., IRRIGATE/RETURN 1) mode. As shown in FIGS. 8 and 15, when the platen 86 is situated in the RETURN 1 mode, the auxiliary tubings 34 and 36 are both placed in vertical alignment with one of the second surface areas 112, pinching close the tubings 34 and 36, while the recipient set tubing 62 and (in the second embodiment) the primary tubing 28 are placed in vertical alignment with separate ones of the first surface areas 110, opening the tubings 62 and 28.

In the next step of the plasmapheresis procedure, the spiked end portion 69 of another one of the inlet lines 68 (see FIG. 1) is inserted into the outlet port 116 of the separated first container 24, as shown in phantom lines in FIG. 1. As is also shown in FIG. 1, the inlet ports 116 of each container 24 and 26 include a normally closed membrane 118 which is pierced by the spiked end portion 69 to open the port 116.

By closing the roller clamp 72 (controlling saline flow) and by opening the roller clamp 74, red cells in the separated first container 24 can be returned to the donor through the manifold means 38 and primary tubing 28 without changing the position of the plate 86 from the RETURN 1 mode. After the red cells in the first container 24 have been returned to the donor, and still maintaining the platen 86 in the RETURN mode 1, the heretofore opened roller clamp 74 (controlling red cell flow) is closed and the heretofore closed roller clamp 72 (controlling saline flow) is opened to again flush traces of red cells from the manifold means 38 and the primary tubing 28.

The next step in the plasmapheresis procedure is to collect an additional unit of whole blood in the second collection container 26. To accomplish this step, the roller clamp 72 (controlling saline flow) is closed, and the platen 86 is moved (to the right in the FIGS. 3 through 10 embodiment and clockwise in the FIGS. 11 through 17 embodiment) to the position identified as the COL 2 (i.e., COLLECT 2) mode. As shown in FIGS. 9 and 16, the first auxiliary tubing 34 and the recipient set tubing 62 are each placed into vertical alignment with separate ones of the second surface areas 112, pinching close the tubings 34 and 62, while the second auxiliary tubing 36 (associated with the second collection container 26) and (in the second embodioment) the primary tubing 28 are each brought into alignment with separate ones of the first surface areas 110, opening the tubings 28 and 36. Blood can now flow from the donor into only the second container 26.

After whole blood has been collected in the second container 26, the second auxiliary tubing 36 is sealed closed by the use of the pair of hand seal clips or by the formation of a hermetic, snap-apart seal. The second auxiliary tubing 36 is then severed at the closure point to separate the second container 26 from the assembly 22 for processing into plasma and red cells. As before, the plasma is expressed from the container 26, leaving the red cells.

While the whole blood in the separated second container 26 is being processed, the platen 86 is moved (further to the right in the FIGS. 3 through 11 embodiment and further clockwise in the FIGS. 11 through 17 embodiment) to the position identified as the RETURN 2 (i.e., IRRIGATE/RETURN 2) mode. As shown in FIGS. 10 and 17, when the platen 86 is in the RETURN 2 mode, both auxiliary tubings 34 and 36 are placed in vertical alignment with one of the second surface area 112, pinching close the tubings 34 and 36, while the recipient set tubing 62 and (in the second embodiment) the primary tubing 28 are placed in vertical alignment with separate ones of the first surface areas 110, opening the tubings 62 and 28. A flow of saline through the manifold means 38 can thus be established by opening the roller clamp 72.

The final step in the procedure begins. The spiked end portion 71 of the remaining inlet line 70 of the recipient set 60 is inserted into an outlet port 116 of the second container 26, thereby opening the associated membrane 118. By closing the roller clamp 72 (terminating the flow of saline) and by opening the roller clamp 76 (controlling red cell flow), red cells in the second container 26 can be returned to the donor.

The plasmapheresis procedure is then concluded. The locking mechanisms 89 can be released and the housing 88 moved to its inoperative position. The manifold means 38 and associated tubings 28, 34, 36, and 62 can be removed from the indentation 84 and discarded along with the rest of the assembly 22.

From the foregoing, it can be appreciated that the flow control device 10 which embodies the features of the invention obviates a need for plurality of hemostats, roller clamps, or the like. The device 10 permits complex, repetitive valving functions throughout a plurality of flow modes to be made from a convenient, centralized location. The device performs these valving functions in a straightforward manner, without introducing complicated, unwieldy, or leak-prone devices into the flow system.

The device 10 is also extremely adaptable. It can be readily incorporated into virtually any fluid system, regardless of the complexity of the system or the complexity of the valving functions required to operate the system.

Various of the features of the invention are set forth in the following claims.

I claim:

1. A flow control device for a flexible conduit comprising
a first member,
means for releasably securing a length of flexible conduit on said first member,
a second member including a housing and a platen movably mounted on said housing,
means for mounting said second member housing in an operative position on said first member, in which position the secured conduit is disposed between said first member and said movable platen of said second member, and
means on said movable platen operative, in response to displacement of said movable platen when said second member housing is in said operative position, for selectively pinching close the secured conduit between said movable platen and said first member.

2. A flow control device according to claim 1 wherein said movable platen of said second member is operative for movement transversely of said second member housing.

3. A flow control device according to claim 2 wherein the path of movement of said movable platen extends generally transversely of the axis of the secured conduit when said second member housing is in said operative position.

4. A flow control device according to claim 1 wherein said movable platen of said second member is operative for rotation relative to said second member housing.

5. A flow control device according to claim 1 or 2 or 4 wherein said conduit pinching means includes cam means operative, when said movable portion is in a first platen, for engaging the secured conduit to pinch the conduit between said cam means and said first member, thereby pinching close the secured conduit, and, when said movable platen is moved from said first position toward a second position, for disengaging the secured conduit.

6. A flow control device according to claim 5 wherein said mounting means includes means attaching said second member on said first member housing for movement between an inoperative position, in which said movable platen generally faces away from the secured conduit, and said operative position, in which said movable platen faces the secured conduit.

7. A flow control device according to claim 6 wherein said attachment means includes a hinge attaching said second member on said first member housing for movement between said inoperative position and said operative position.

8. A flow control device according to claim 1 or 2 or 4 wherein said conduit pinching means includes cam means on said platen operative, in response to movement of said platen relative to said housing, for selectively engaging the secured conduit between said cam means and said first member to pinch close the conduit.

9. A flow control device according to claim 8 wherein said platen is movable on said housing between spaced first and second positions, wherein said cam means is operative for engaging the secured conduit in response to movement of said platen toward one of said first and second positions and for disengaging the conduit in response to movement of said platen toward the other one of said positions.

10. A flow control device according to claim 1 wherein said means for releasably securing a length of conduit on said first member includes means for releasably securing at least two lengths of flexible conduit on said first member, and
wherein said conduit pinching means on said movable platen is operative, in response to movement of said movable platen when said second member housing is in said operative position, for selective pinching close at least one of the secured conduits between said movable platen and said first member.

11. A flow control device according to claim 10 wherein said conduit pinching means is operative for pinching close more than one of the secured conduits at the same time.

12. A flow control device according to claim 10 or 11 wherein said conduit pinching means is operative for pinching close at least one of the secured conduits without pinching close other secured conduits.

13. A flow control device according to claim 12 wherein said movable platen of said second member housing is operative for movement transversely of said second member housing.

14. A flow control device according to claim 13 wherein the path of movement of said movable platen extends generally transversely of the axis of some of the secured conduits when said second member housing is in said operative position.

15. A flow control device according to claim 12 wherein said movable platen of said second member is operative for rotation relative to said second member housing.

16. A flow control device according to claim 12 wherein said movable platen of said second member housing is operative for movement between spaced first and second positions, and
wherein said conduit pinching means includes cam means operative for engaging at least one of the secured conduits in response to movement of said movable platen toward one of said first and second positions, thereby pinching close the engaged conduit, and for subsequently disengaging the conduit in response to movement of said movable platen toward the other one of said positions.

17. A flow control device according to claim 12 wherein said mounting means includes means attaching said second member on said first member housing for movement between an inoperative position, in which said movable platen generally faces away from the secured conduits, and said operative position, in which said movable platen faces the secured conduits.

18. A flow control assembly for flexible fluid conduits comprising
first means attachable to two or more flexible fluid conduits and operative for establishing flow communication between the attached conduits, and
a flow control device comprising
a first member,
means for releasably securing on said first member said first means and the conduits attached thereto,
a second member including a movable portion,
means for mounting said second member on said first member, in which position the conduits which are attached to said first means are disposed between said first means and said movable portion, and
means on said movable portion operative, in response to movement of said movable portion when said second member is in said operative position, for selectively pinching close at least one of the attached conduits between said movable portion and said first member.

19. A flow control assembly according to claim 18 wherein said conduit pinching means is operative for pinching close more than one of the secured conduits at the same time.

20. A flow control assembly according to claim 18 or 19 wherein said conduit pinching means is operative for pinching close at least one of the secured conduits without pinching close other secured conduits.

21. A flow control assembly according to claim 20 wherein said movable portion of said second member is operative for movement transversely of the remaining portion of said second member.

22. A flow control assembly according to claim 20 wherein the path of movement of said movable portion extends generally transversely of the axis of some of the secured conduits when said second member is in said operative position.

23. A flow control assembly according to claim 20 wherein said movable portion of said second member is operative for rotation relative to the remaining portion said second member.

24. A flow control assembly according to claim 20 wherein said movable portion of said second member is operative for movement between spaced first and second positions, and
wherein said conduit pinching means includes cam means operative for engaging at least one of the secured conduits between said cam means and said first member in response to movement of said movable portion toward one of said first and second positions, thereby pinching close the engaged conduit, and for subsequently disengaging the conduit in response to movement of said movable portion toward the other one of said positions.

25. A flow control assembly according to claim 20 wherein said mounting means includes means attaching said second member on said first member for movement between an inoperative position, in which said movable portion generally faces away from the secured conduits, and said operative position, in which said movable portion faces the secured conduit.

26. A flow control assembly according to claim 25 wherein said movable portion of said second member includes a platen,
wherein the remaining portion of said second member includes a housing on which said platen is movably mounted, and
wherein said mounting means attaches said housing on said first member for movement between said operative and inoperative positions.

27. A flow control assembly according to claim 26 wherein said conduit pinching means includes cam means on said platen operative, when said housing is in said operative position, for selectively pinching close at least one secured conduit between said cam means and said first member in response to movement of said platen.

28. A flow control assembly according to claim 27 wherein said platen is movable on said housing between spaced first and second positions,
wherein said cam means is operative for engaging at least one of the secured conduits between said cam means and said first member in response to movement of said platen toward one of said first and second positions, thereby pinching close the engaged conduit, and for subsequently disengaging the conduit in response to movement of said platen toward the other one of said positions.

29. A plasmapheresis assembly comprising
a primary conduit including, at one end thereof, a phlebotomy needle,
first and second blood collection containers,
first and second auxiliary conduits respectively attached in flow communication with said collection containers,
a manifold interconnecting said primary conduit with said first and second auxiliary conduits, and
a flow control device comprising
a first member,
means for releasably securing said manifold and a portion of said attached conduits on said first member,
a second member including a movable portion, and
means for mounting said second member in an operative position on said first member, in which position said secured portions of said primary and said auxiliary conduits are disposed between said first means and said movable portion, and
means on said movable portion operative, in response to movement of said movable portion when said second member is in said operative position, for individually and selectively pinching close each of said auxiliary conduits between said first means and said movable member.

30. A plasmapheresis assembly according to claim 29 wherein said manifold includes
a main passage having an end attached in flow communication with said primary conduit and an end normally open to communication with the atmosphere and accommodating attachment to a recipient set for conducting fluids into said main passage,
a pair of branch passages each communicating with said main passage intermediate said ends thereof and attached in flow communication with a respective one of said first and second auxiliary conduit means, and
plug means removably insertable into said open end of said main passage for sealing said open end while simultaneously blocking flow communication between said branch passages through said main passage.

31. A plasmapheresis assembly according to claim 30 wherein said conduit securing means is operative for releasably securing on said first member a portion of the recipient set which is attached to said manifold, and
wherein said conduit pinching means is operative, when said second member is in said operative position, for selectively pinching said recipient set portion close between said movable portion and said first means in response to movement of said movable portion.

32. A plasmapheresis assembly according to claim 29 or 31
wherein said movable portion of said second member is operative for movement transversely of the remaining portion of said second member.

33. A plasmapheresis assembly according to claim 29 or 31
wherein said movable portion of said second member is operative for rotation relative to the remaining portion of said second member.

34. A plasmapheresis assembly according to claim 29 or 31
wherein said conduit pinching means includes cam means operative, when said movable portion is in a first position, for engaging the secured conduit to pinch the conduit between said cam means and said first member, thereby closing the secured conduit, and, when said movable portion is moved from said first position toward a second position, for disengaging the secured conduit.

35. A plasmapheresis assembly according to claim 29 or 31
wherein said mounting means includes means attaching said second member on said first member for movement between an inoperative position, in which said movable portion generally faces away from the secured conduits, and said operative position, in which said movable portion faces the secured conduit.

36. A plasmapheresis assembly according to claim 35
wherein said movable portion of said second member includes a platen,
wherein the other portion of said second member includes a housing on which said platen is movably mounted, and
wherein said mounting means attaches said housing on said first member for movement between said operative and inoperative positions.

37. A plasmapheresis assembly according to claim 36
wherein said conduit pinching means includes cam means on said platen operative for selectively pinching close at least one secured conduit between said cam means and said first member in response to movement of said platen when said housing is in said operative position.

38. A plasmapheresis assembly according to claim 37
wherein said platen is movable on said housing between spaced first and second positions,
wherein said cam means is operative for engaging at least one of the secured conduits between said cam means and said first member in response to movement of said platen toward one of said first and second positions, thereby pinching close the engaged conduit, and for subsequently disengaging the conduit in response to movement of said platen toward the other one of said positions.

* * * * *